United States Patent [19]

Griffith

[11] Patent Number: 4,782,058

[45] Date of Patent: * Nov. 1, 1988

[54] 1,3,4,6,7,11B-HEXAHYDRO-6-PHENYL-2H-PYRAZINO-(2,1-A)ISOQUINOLINES, FOR ANTI-HISTAMINE OR ANTI-DEPRESSION TREATMENT

[75] Inventor: Ronald C. Griffith, Pittsford, N.Y.

[73] Assignee: Pennwalt Corporation, Philadelphia, Pa.

[*] Notice: The portion of the term of this patent subsequent to May 14, 2002 has been disclaimed.

[21] Appl. No.: 129,918

[22] Filed: Dec. 3, 1987

Related U.S. Application Data

[63] Continuation of Ser. No. 727,698, Apr. 26, 1985, abandoned.

[51] Int. Cl.$^4$ ............... C07D 217/24; C07D 217/22; C07D 471/04; A61K 31/495
[52] U.S. Cl. ............... 514/250; 544/344; 546/144; 564/212
[58] Field of Search ............... 514/250; 544/344

[56] References Cited

U.S. PATENT DOCUMENTS 4,162,319  7/1979  Senkert ............... 544/354
4,517,187  5/1985  Griffith ............... 544/354

Primary Examiner—Mark L. Berch
Attorney, Agent, or Firm—Panitch Schwarze Jacobs & Nadel

[57] ABSTRACT

Novel 1,3,4,6,7,11b-hexahydro-6-phenyl-2H-pyrazino[2,1-a]isoquinolines, including a cis-1,3,4,6,7,11b-hexahydro-9-methoxy-2-methyl-6-phenyl-2H-pyrazino[2,1-a]isoquinoline dihydrochloride and cis-1,3,4,6,7,11b-hexahydro-9-hydroxy-2-methyl-6-phenyl-2H-pyrazino[2,1-a]isoquinoline dihydrobromide; useful as anti-histamine and anti-depressant agents.

10 Claims, No Drawings

1,3,4,6,7,11B-HEXAHYDRO-6-PHENYL-2H-PYRAZINO-(2,1-A)ISOQUINOLINES, FOR ANTI-HISTAMINE OR ANTI-DEPRESSION TREATMENT

REFERENCE TO A RELATED APPLICATION

This application is a continuation of U.S. Ser. No. 727,698, filed Apr. 26, 1985, now abandoned.

BACKGROUND OF THE INVENTION

This invention relates to novel 1,3,4,6,7,11b-hexahydro-6-phenyl-2H-pyrazino[2-1,a]isoquinolines with anti-histamine and anti-depressant activity in mammals.

Applicant's U.S. patent application, Ser. No. 435,132, and the related publications, Griffith et al, *J. Med Chem.*, 27, 995–1003 (1984) and Griffith et al, *Acta. Cryst.* C40, 1103–1105 (1984), describe 7-phenyl-1,3,4,6,7,11b-hexahydro-2H-pyrazino[2,1-a]isoquinolines with antihistamine and antidepressant activity.

BRIEF SUMMARY OF THE INVENTION

The compounds of this invention are those of the formula (I)

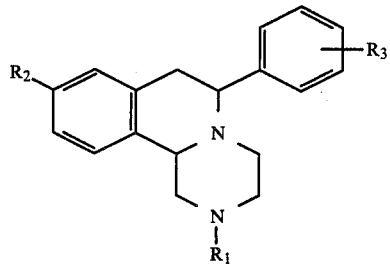

I wherein $R_1$ is hydrogen, $C_1$–$C_7$ alkyl, $C_3$–$C_7$ cycloalkyl or $C_4$–$C_8$ cycloalkylmethyl;

$R_2$ is hydrogen, hydroxy or $C_1$–$C_7$ alkoxy; and $R_3$ is a single or multiple substitution by hydrogen, hydroxy, halogen, $C_1$–$C_7$ alkoxy, $C_1$–$C_7$ alkyl or trifluoromethyl; all stereoisomeric forms thereof, and pharmaceutically acceptable addition salts thereof.

The invention also includes pharmaceutical preparations containing one or more of the above compounds as an active ingredient and methods for administering the pharmaceutical preparations to a human or other mammal in need of anti-histamine (e.g., for allergy treatment) and/or anti-depressant treatment. In addition, it includes processes for making the compounds.

DETAILED DESCRIPTION

Compounds

The compounds of this invention are those of the formula (I)

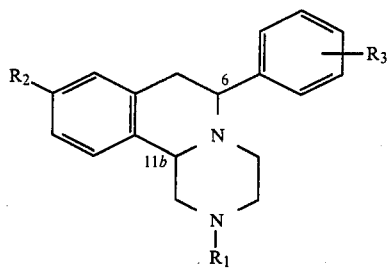

I wherein $R_1$ is hydrogen, $C_1$–$C_7$ alkyl, $C_3$–$C_7$ cycloalkyl or $C_4$–$C_8$ cycloalkylmethyl;

$R_2$ is hydrogen, hydroxy or $C_1$–$C_7$ alkoxy; and $R_3$ is a single or multiple substitution by hydrogen, hydroxy, halogen, $C_1$–$C_7$ alkoxy, $C_1$–$C_7$ alkyl or trifluoromethyl; all stereoisomeric forms thereof, and pharmaceutically acceptable addition salts thereof.

Positions 6 and 11b in formula I are designated accordingly.

The notation, "$C_1$–$C_7$ alkyl", refers to an alkyl group of one to seven carbon atoms, straight or branched. The notation, "$C_1$–$C_7$ alkoxy", refers to an alkoxy group of one to seven carbon atoms, straight or branched. The notation, "$C_3$–$C_7$ cycloalkyl", refers to a cycloalkyl group of three to seven carbon atoms, and "$C_4$–$C_8$ cycloalkylmethyl" refers to a cycloalkyl group, of three to seven carbon atoms, joined to a methylene group, the methylene group providing the point of attachment to the remainder of the compound. "Halogen" means chlorine, bromine, fluorine, or iodine. Multiple substitution of an $R_3$ moiety means two to five substitutions. Each $R_3$ substituent in an embodiment of the compound of formula I can be selected independently of any nature of the other $R_3$ substituent. In the preferred compounds, $R_3$ is either a single or double substitution. Especially preferred compounds are those in which $R_1$ is hydrogen or $C_1$–$C_7$ alkyl, $R_2$ is methoxy, hydroxy or hydrogen, and $R_3$ is a single or double substitution by hydrogen, hydroxy, halogen, methoxy, methyl or trifluoromethyl.

The stereochemistry at positions 6 and 11b can be cis or trans. The compounds of the invention may therefore occur in the following stereoisomeric forms: as the cis diastereoisomeric form, as either of the two optically active enantiomeric forms that comprise the cis diastereoisomeric form, as the trans diastereoisomeric form, or as either of the two optically active enantiomeric forms that comprise the trans diastereoisomeric form. The invention includes all the stereoisomeric forms thereof.

Formation of Compounds Where $R_2$ Is Alkoxy

Using Methods A through F below, all the compounds of the invention in which $R_2$ is $C_1$–$C_7$ alkoxy can be formed. Methods A through F also constitute the preferred procedure for compounds in which $R_2$ is $C_1$–$C_7$ alkoxy and $R_1$ is either methyl or $C_3$–$C_7$ cycloalkyl. If, however, it is desired to have $R_2$ as $C_1$–$C_7$ alkoxy and $R_1$ as either hydrogen, $C_2$–$C_7$ alkyl or $C_4$–$C_8$ cycloalkylmethyl, then the preferred approach is to use Methods A through F to make the corresponding compound with $R_1$ as methyl, and then use Method I to demethylate $R_1$ to hydrogen, and, if desired, use Method J to convert $R_1$ to $C_2$–$C_7$ alkyl or $C_4$–$C_8$ cycloalkylmethyl.

Method A

A 1,2-Diphenylethylamine of the formula II

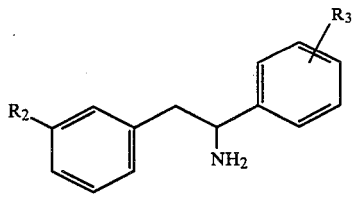

(where $R_2$ is $C_1$-$C_7$ alkoxy and $R_3$ is defined above) is acylated with chloroacetyl chloride in the presence of triethylamine in an inert solvent to produce the corresponding chloroacetyl amide of formula III

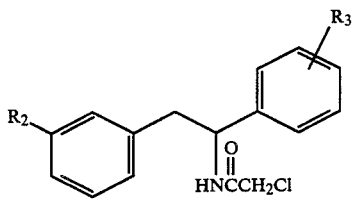

Method B

An amide of formula III (where $R_2$ is $C_1$-$C_7$ alkoxy and $R_3$ is defined above) is cyclized under Bischler-Napieralski conditions with an appropriate acid catalyst such as phosphorus pentoxide in an inert solvent to give the corresponding 1-chloromethyl-3,4-dihydro-3-phenylisoquinoline of formula IV

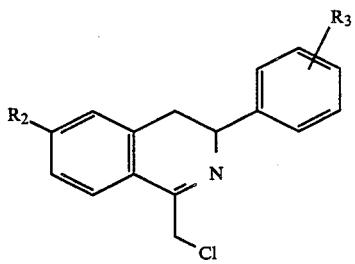

Method C

A compound of formula IV (where $R_2$ is $C_1$-$C_7$ alkoxy and $R_3$ is defined above) is aminated with an amine of the formula $R_1$—$NH_2$ (where $R_1$ is defined above) in alcoholic media.

Method D

The imine group of the product of Method C is reduced, preferably by catalytic hydrogenation, providing the 1-aminomethyl-1,2,3,4-tetrahydro-3-phenylisoquinoline of formula V

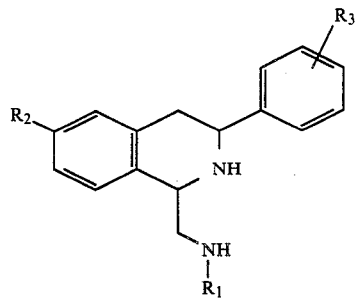

Method E

A compound of formula V (where $R_2$ is $C_1$-$C_7$ alkoxy and $R_3$ is defined above) is cyclized with diethyl oxalate to form a compound of the formula VI

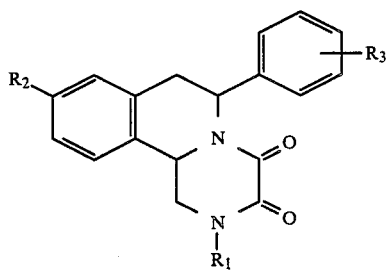

having the corresponding $R_2$ and $R_3$ groups.

Method F

A cyclized diamide compound that is the product of Method E is reduced with a complex hydride reducing agent, preferably borane in tetrahydrofuran, thereby producing the corresponding compound of formula I. Reaction conditions are illustrated in Example 1.

Formation of Compounds Where $R_2$ Is Not Alkoxy

Using Methods G and H, below, all the compounds of the invention in which $R_2$ is hydrogen or hydroxy can be formed. If, however, it is desired to have $R_2$ as either hydrogen or hydroxy and $R_1$ as either hydrogen, $C_2$-$C_7$ alkyl or $C_4$-$C_8$ cycloalkylmethyl, then the preferred approach is to make the compound with the desired $R_2$ and $R_3$ groups but with $R_1$ as methyl, then demethylate $R_1$ to hydrogen according to Method I and then, if desired, convert $R_1$ to either $C_2$-$C_7$ alkyl or $C_4$-$C_8$ cycloalkylmethyl using Method J. Method G is the preferred procedure for making compounds in which $R_2$ is hydroxy and $R_1$ is either methyl or $C_3$-$C_7$ cycloalkyl. Method G in combination with Method H is the preferred procedure for compounds in which $R_2$ is hydrogen and $R_1$ is either methyl or $C_3$-$C_7$ cycloalkyl.

Method G

A compound of formula I in which $R_2$ is $C_1$-$C_7$ alkoxy (but preferably, methoxy) is converted to the corresponding compound in which $R_2$ is hydroxy by ether cleavage. For example, treatment of the compound of formula I in which $R_1$ is methyl, $R_2$ is methoxy, and $R_3$ is hydrogen, with HBr (preferably 48% HBr) results in the compound of formula I in which $R_1$ is methyl, $R_2$ is hydroxy, and $R_3$ is hydrogen. Reaction conditions are illustrated in Example 2.

Method H

A compound of formula I in which $R_2$ is hydroxy is converted to the corresponding compound of formula I in which $R_2$ is hydrogen by treatment with 5-chloro-1-phenyl-1H-tetrazole to give the tetrazole-substituted ether (i.e., $R_2$ is replaced by $OR_4$ where $R_4$ is 1-phenyl-1H-tetrazol-5-yl), followed by catalytic hydrogenolysis.

For example, treatment of the compound of formula I in which $R_1$ is methyl, $R_2$ is hydroxy, and $R_3$ is hydrogen, with 5-chloro-1-phenyl-1H-tetrazole in dimethylsulfoxide in the presence of potassium carbonate gives the tetrazole ether which, upon hydrogenation over palladium catalyst in alcohol, provides the compound of formula I in which $R_1$ is methyl, $R_2$ is hydrogen, and $R_3$ is hydrogen. Reaction conditions are illustrated in Example 3.

Formation of Compounds Where $R_1$ Is Not Methyl

Method I

For the preparation of compounds where $R_1$ is hydrogen it is possible to dealkylate a compound of formula I (preferably where $R_1$ is methyl), preferably by treatment with methylchloroformate/hydrazine, as described by Brine et al (*Org. Prep. Proc. Int.* 8, 103–106 (1976), to provide compounds of formula I where $R_1$ is hydrogen.

Method J

A dealkylated compound resulting from Method I may be converted to a compound of formula I where $R_1$ is $C_2-C_7$ alkyl or $C_4-C_8$ cycloalkylmethyl preferably by acylation at the secondary nitrogen atom with the corresponding acyl halide (which results in $R_1$ being replaced by COR where R is $C_1-C_6$ alkyl or $C_3-C_7$ cycloalkyl) followed by hydride reduction of the resulting amide, preferably with borane in tetrahydrofuran.

Formation of Alkoxy-substituted 1,2-diphenylamines

An alkoxy-substituted 1,2-diphenylethylamine of formula II can be prepared in four steps as follows: (1) 3-alkoxybenzyl chloride is converted to 3-alkoxybenzylmagnesium chloride by treatment with magnesium in ether. (2) Reaction of 3-alkoxybenzylmagnesium chloride with a cyanophenyl compound of formula VII

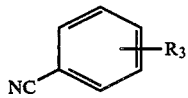

VII wherein $R_3$ represents single or multiple substitution of hydrogen, hydroxy, halogen, $C_1-C_7$ alkoxy, $C_1-C_7$ alkyl or trifluoromethyl provides the corresponding 1,2-diphenylethanone of formula VIII,

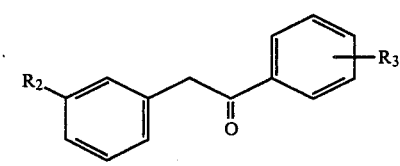

VIII where $R_2$ is $C_1-C_7$ alkoxy. (3) Treatment of a compound of formula VIII with hydroxylamine hydrochloride in alcohol. (4) Catalytic reduction of the resultant oxime with hydrogen over palladium on carbon in an alcoholic solvent produces the desired substituted 1,2-diphenylethylamine of formula II.

For example, in step (2), treatment of 3-methoxybenzylmagnesium chloride with benzonitrile at 0° in ether solution gives 1-phenyl-2-(3-methoxyphenyl)ethanone which in step (3) is treated with hydroxylamine hydrochloride to form an oxime which in step (4) is reduced with hydrogen over 10% Pd on carbon gives 1-phenyl-2-(3-methoxyphenyl)ethylamine.

Preparation of the Diastereoisomeric and Enantiomeric Forms of the Compounds of Formula I To produce the cis-diastereoisomeric form of a compound of formula I substantially free of its trans-diastereoisomeric form, the above procedures are followed, providing that Method D is carried out using a catalytic reduction as opposed to a non-catalytic reduction. The catalytic reduction results in a preponderance of the cis-diastereoisomeric form of the compound of formula V; [an optional step at this point is to eliminate the trans-diastereoisomeric form of the compound of formula V by silica gel chromatography, using 5% ammonium methanol/chloroform as the eluent.] Further processing of the cis-diastereoisomeric form of formula V, by any of the recommended combinations of Methods E through J, will result in the cis-diastereoisomeric form of a compound of Formula I substantially free of its trans-diastereoisomeric form.

The trans-diastereoisomeric form of the compound of formula V can be prepared by performing Method D with either catalytic or non-catalytic (e.g. using sodium borohydride) reduction, isolating the trans-diastereoisomeric form of the compound of formula V by silica gel chromatography using 5% ammonium methanol/chloroform as the eluent, and further processing according to one of the recommended combination of methods selected from Methods E through J.

Each purified diastereoisomeric form can be resolved into its component enantiomers by conventional methods for separating a racemic mixture into its components, so that each of its two enantiomeric forms is substantially free of the other. An example of such a method is the reaction of the racemic mixture with a stoichiometric amount of an optically active acid, such as (+)- or (−)-tartaric acid, (+)- or (−)-dibenzoyl tartaric acid, (+)- or (−)-monomethyl tartrate, or other derivative of tartaric acid. The reaction is carried out in a solvent in which the resulting salt of one of the enantiomers of the formula I compound has a different solubility than the resulting salt of the other enantiomer. Methanol, ethanol, or mixtures thereof, are preferred solvents. The preferentially insoluble enantiomer salt is then recovered and converted to the free base by conventional means. If the preferentially insoluble enantiomer salt is still contaminated by an undesirably large amount of the other enantiomer salt, the reaction with tartaric acid or its derivative and the subsequent recovery and conversion steps may be repeated.

Pharmaceutically Acceptable Addition Salts

Pharmaceutically acceptable acid addition salts of the 1,3,4,6,7,11b-hexahydro-6-phenyl-2H-pyrazino[2,1-a]isoquinoline bases of this invention are prepared by treating a compound of formula I with any one of various mineral and organic acids that form non-toxic addition salts having pharmaceutically acceptable anions. Such salts are the hydrochloride, hydrobromide, hydroiodide, sulfate or bisulfate, phosphate or acid phosphate, acetate, lactate, maleate, fumarate, citrate or acid citrate, tartrate or bitartrate, succinate, gluconate, saccharate, methanesulfonate, benzenesulfonate or p-toluenesulfonate. For instance, the salt-formation step may be carried out by using an essentially equimolar amount of the appropriate acid in an aqueous solvent medium or in a suitable organic solvent such as ethanol or methanol. Upon either standing or careful evaporation of the solvent, the solid salt product is readily obtained.

Anti-histamine Activity

A particularly useful compound with regard to anti-histamine activity is the title compound of Example 2 (i.e., the cis-diastereoisomeric form of the compound of formula I in which $R_1$ is methyl, $R_2$ is hydroxyl, and $R_3$ is hydrogen).

That compound was assayed for anti-histamine activity by measuring its ability to inhibit the binding of 3H-pyrilamine to homogenated rat cerebral tissue. (3H-Pyrilamine is a radioligand that is used to characterize histamine $H_1$-receptors in brain tissue.) Assay conditions were essentially those of V. T. Tran et al, Proc. Nat'l. Acad. Sci. (USA) 75, p. 6290–6294 (1978). The $IC_{50}$ (50% inhibitory concentration) of the compound was $2.5 \times 10^{-7}$M.

Anti-depressant Activity

A particularly useful compound with respect to anti-depressant activity is the title compound of Example 1 (i.e., the cis-diastereoisomeric form of the compound of formula I in which $R_1$ is methyl, $R_2$ is methoxy, and $R_3$ is hydrogen). That compound was tested for antidepressant activity by measuring its ability to inhibit tetrabenazine-induced ptosis in mice.

Male CF-1 mice weighing 19–32 grams were housed for a minimum of 5 days under a 12 hour light/dark (6 am/6 pm) schedule at 70°–74° F. and relative humidity of 30–50%. Food and water were available ad libitum until the time of administration of test compounds. Mice in groups of ten were orally administered (via gastric intubation) either the control solution (distilled water, 10 ml/kg) or the test compound. The test compound was either dissolved in distilled water or suspended in distilled water containing a drop of polyoxyethylene 20 sorbitan monooleate, sold under the trademark, Tween 80. After fifteen minutes, a dose of 10 ml/kg of a solution of tetrabenazine (as its methane sulfonate salt) in distilled water (4 mg/ml) was administered by intravenous injection. The degree of palpebral closure (ptosis) was determined 30, 60, 90, 120, and 150 minutes after administration of the tetrabenazine solution. Each mouse was held by the tail with the front paws supported by a thin wood applicator stick (or pencil) for approximately 10 seconds for each determination. The ptosis was rated on scale of 0 to 4 with each number representing a degree of eye closure:
0=Eyes fully open-no ptosis
1=Eyelids closed one-quarter
2=Eyelids closed one-half
3=Eyelids closed three-quarters
4=Eyelids fully closed The lowest active dose (LAD) of the title compound of Example 1, in this assay for antidepressant activity, was 20 mg/kg.

ILLUSTRATIONS AND EXAMPLES

The following specific non-limiting Illustrations (of synthesis of intermediates) and Examples (of compounds of the invention) are provided.

ILLUSTRATION 1

Preparation of 1-phenyl-2-(3-methoxyphenyl)ethanone

3-Methoxybenzyl chloride (190 g, 1.21 mol) was added dropwise with stirring to a suspension of magnesium turnings (30.0 g, 1.24 mol) in ether (4 L) under nitrogen at a rate sufficient to maintain reflux and then the mixture was refluxed for an additional 4 hrs. The mixture was cooled, benzonitrile (113.4 g, 1.1 mol) added, and the mixture was then heated to reflux for 12 hrs. The mixture was allowed to cool, methanol (197.3 ml) was added dropwise, and the mixture was stirred for 1 hr. Two liters of 10% HCl was added to the mixture, which was then stirred for an additional 1 hr after which the ether layer was separated and dried over $MgSO_4$. Evaporation of the solvent gave 253 g of a yellow oil which was vacuum distilled (163°–170°/0.1 mm) to give 202 g (87%) of 1-phenyl-2-(3-methoxyphenyl)ethanone as a colorless oil.

ILLUSTRATION 2

Preparation of 1-phenyl-2-(3-methoxyphenyl)ethanone oxime

A solution of hydroxylamine hydrochloride (185.5 g, 2.67 mol) water (0.3 L) was added with stirring to a solution of 1-phenyl-2-(3-methoxyphenyl)ethanone (187 g, 0.89 mol) in 95% ethanol (1.4 L). Then, 0.3 L of 20% NaOH was added, with stirring, to the resulting mixture. The mixture was heated to reflux for 2 hrs, cooled, and the alcohol was evaporated with a water aspirator. The aqueous residue was extracted with ether ($3 \times 500$ ml). The combined ether extracts were dried over $MgSO_4$ and evaporated to provide a solid residue which was then recrystallized from cyclohexane (1 L) to provide 165.5 g (82%) of 1-phenyl-2-(3-methoxyphenyl)ethanone oxime. An analytical sample, recrystallized from ethylacetate/cyclohexane, had mp. 72°–73° C.

ILLUSTRATION 3

Preparation of 1-phenyl-2-(3-methoxyphenyl)ethylamine hydrochloride

Two separate solutions of 1-phenyl-2-(3-methoxyphenyl)ethanone oxime (82.0 g, 0.36 mol) in a mixture of methanol (1.5 L) and 10% HCl (25 ml) were each hydrogenated in a Parr apparatus over 5.0 g of 10% Pd/C catalyst until hydrogen uptake ceased (1 hr.). The catalyst was removed from each solution by filtration and the filtrates of the two solutions were combined. The solvent was evaporated and the residue was dissolved in ca. 200 ml of methanol, 800 ml of ether was added, and the resulting suspension yielded 82.0 g of white solid. The filtrate was evaporated, the residue was dissolved in ca. 100 ml of isopropanol, and 600 ml of ether was added. The resulting solution yielded 84.0 g of solid which was combined with the 82.0 g of solid to give 166 g (86%) of 1-phenyl-2-(3-methoxyphenyl)ethylamine hydrochloride. An analytical sample recrystallized from ethanol/ether and vacuum dried had mp. 210°–211° C.

ILLUSTRATION 4

Preparation of 1-substituted phenyl-2-(3-methoxyphenyl)ethylamines

By employing the procedures described in Illustrations 1 to 3, but substituting the appropriate substituted benzonitrile for benzonitrile in Illustration 1, compounds of formula II may be obtained, where $R_2$ is methoxy, and $R_3$ is defined above and is, for example, 2-chloro, 3-chloro, 4-chloro, 2-bromo, 3-bromo, 4-bromo, 2-fluoro, 3-fluoro, 4-fluoro, 2-methoxy, 3-methoxy, 4-methoxy, 2-hydroxy, 3-hydroxy, 4-hydroxy, 2-methyl, 3-methyl, 4-methyl, 2-trifluoromethyl, 3-trifluoromethyl, 3-trifluoromethyl, 4-trifluoromethyl, 3,4-dichloro, 3,5-dichloro, 2,6-dichloro, 2,3-difluoro, 2,4-difluoro, 2,5-difluoro, 2,6-difluoro, 3,4-difluoro, 2,3-dimethoxy, 2,4-dimethoxy, 2,6-dimethoxy, 3,4-dimethoxy, 3,5-dimethoxy, 2,3,4-trimethoxy, 2,4,6-trimethoxy, 3,4,5-trimethoxy, 2,5-dimethyl, 2-chloro-6-methyl, or 3-chloro-4-methyl. $R_2$ can be changed to $C_2$–$C_7$ alkoxy by substituting the appropriate 3-alkoxybenzyl chloride (for example, 3-ethoxybenzyl chloride, or 3-heptoxybenzyl chloride) for 3-methoxybenzyl chloride in Illustration 1.

ILLUSTRATION 5

Preparation of N-chloroacetyl-1-phenyl-2-(3-methoxyphenyl)ethylamine

Triethylamine (254.9 g, 2.5 mol) was added with stirring to a solution of 1-phenyl-2-(3-methoxyphenyl)ethylamine hydrochloride (166.0 g, 0.63 mol) in chloroform (4 L) under nitrogen at 0° C. Then chloroacetyl chloride (142.2 g, 1.26 mol) was added dropwise over a period of 2 hrs. The resulting mixture was stirred at ambient temperature (about 25° C.) for 16 hrs, washed with 10% HCl (3×1 L) and water (1 L), and then the organic phase was dried over MgSO$_4$. Evaporation of the solvent gave a dark oily residue which was dissolved in cyclohexane (2 L). Upon standing, the resulting solution gave solid crystals which were collected by filtration and dried to give 142.5 g of N-chloroacetyl-1-phenyl-2-(3-methoxyphenyl)ethylamine. A sample recrystallized twice from cyclohexane had a mp. 104°–105° C.

ILLUSTRATION 6

Preparation of 1-chloromethyl-3,4-dihydro-6-methoxy-3-phenylisoquinoline hydrochloride Solid N-chloroacetyl-1-phenyl-2-(3-methoxyphenyl)ethylamine (72.0 g, 0.23 mol) was added with stirring to a suspension of phosphorus pentoxide (261.1 g, 1.84 mol) in xylene (6 L) maintained under nitrogen at reflux, and the resulting mixture was refluxed for 1 hr, after which it was allowed to cool to ambient temperature. The xylene was decanted off and the residue was cooled to 0° C. Ice cold water (4 L) was added to the residue, and the resulting solution was then basified to pH 11 with 50% NaOH, and then extracted, first with ether (1 L) and then with chloroform (2×750 ml). The combined organic extracts were dried over MgSO$_4$, evaporated to a dark oil which was dissolved in a mixture of acetone (200 ml) and ether (100 ml) and then acidified with HCl gas. Upon standing, the treated extracts yielded yellowish solid crystals, which were collected by filtration to give 48.8 g (64%) of 1-chloromethyl-3,4-dihydro-6-methoxy-3-phenylisoquinoline hydrochloride. An analyticl sample recrystallized from acetone had a mp. 174°–175° C.

ILLUSTRATION 7

Preparation of cis- and trans-6-methoxy-1-(methylamino)methyl-3-phenylisoquinoline 1-Chloromethyl-3,4-dihydro-6-methoxy-3-phenylisoquinoline hydrochloride (20.0 g, 0.06 mol) was added with stirring to a solution of monomethylamine (140 ml) in methanol (500 ml) at 0° C. under nitrogen. The resulting mixture was allowed to warm to ambient temperature and then stirred for 16 hrs at ambient temperature. The mixture was then poured into a pressure bottle and hydrogenated in a Parr apparatus over 5% palladium on carbon catalyst for 3 hrs. The catalyst was removed by filtration and the solvent evaporated to provide a mixture of the cis and trans diastereoisomers of 6-methoxy-1-(methylamino)methyl-3-phenylisoquinoline as the amine bases [the ratio, cis:trans, was ca. 90:10.] An aliquot of the mixture was purified by silica gel chromatography using 5% ammonium methanol/chloroform as the eluent, in order to eliminate the trans diastereoisomer, and was then characterized by its NMR spectrum in CDCl$_3$ (60 MHz) δ 7.6–6.5 (8H, m, aromatics); 4.2 (1H, m); 3.95 (1H, dd, J=8.6); 4.7 (3H, s, OCH$_3$); 3.3–2.6 (3H, m); 2.4 (3H, s, N-CH$_3$); 1.73 (2H, br, s, CH$_2$).

ILLUSTRATION 8

Preparation of 6-alkoxy-1-(alkylamino)methyl-3-phenylisoquinolines

Using the procedures described in the above Illustrations, but substituting an appropriate amine (for example, one made according to Illustration 4) for 2-(3-methoxyphenyl)-1-phenylethylamine when it is necessary to select an appropriate $R_2$ and/or $R_3$ group, and substituting the amine $R_1$—NH$_2$ [where, for example, $R_1$ is hydrogen, ethyl, propyl, butyl, hexyl, heptyl, cyclopropyl, cyclobutyl, cyclopentyl, cyclohexyl, cycloheptyl, cyclopropylmethyl, cyclobutylmethyl, cyclopentylmethyl, cyclohexylmethyl, or cycloheptylmethyl] for monomethylamine (as for example, in Illustration 7) when it is necessary to select an appropriate $R_1$ group, will result in the compound of formula V having the corresponding $R_1$, $R_2$ and $R_3$ groups.

ILLUSTRATION 9

Preparation of cis-1,3,4,6,7,11b-hexahydro-9-methoxy-2-methyl-6-phenyl-2H-pyrazino[2,1-a]isoquinoline-3,4-dione A stirred solution of crude cis-6-methoxy-1-(methylamino)methyl-3-phenylisoquinoline (23.0 g, 0.08 mol), prepared using the procedure of Illustration 7 [but without the chromatographic step used to prepare the aliquot for NMR analysis in Illustration 7], and diethyl oxalate (24.1 g, 0.16 mol) in toluene (500 ml) was refluxed for 24 hrs. Upon cooling, the solution yielded a crystalline solid of which 6.0 g was collected by filtration. The volume of solution was reduced to 150 ml and the mixture was refluxed an additional 8 hrs. Upon filtration, 8 g of white solid was obtained for a total of 14 g of cis-1,3,4,6,7,11b-hexahydro-9-methoxy-2-methyl-6-phenyl-2H-pyrazino[2,1-a]isoquinoline-3,4-dione. An analytical sample recrystallized from 95% ethanol had mp. 216°–217° C. Following the same procedure and replacing cis-6-methoxy-1-(methylamino)methyl-3-phenylisoquinoline with trans-6-methoxy-1-(methylamino)methyl-3-phenylisoquinoline, trans-1,3,4,6,7,11b-hexahydro-9-methoxy-2-methyl-6-phenyl-2H-pyrazino[2,1-a]isoquinoline-3,4-dione may be obtained.

PREPARATION OF THE COMPOUNDS OF FORMULA 1

Example 1

Preparation of cis-1,3,4,6,7,11b-hexahydro-9-methoxy-2-methyl-6-phenyl-2H-pyrazino[2,1-a]isoquinoline dihyrochloride Cis-1,3,4,6,7,11b-hexahydro-9-methoxy-2-methyl-6-methyl-2H-pyrazino[2,1-a]isoquinoline-3,4-dione (16.0 g, 0.04 mol) was added with stirring to a solution of 1M borane in tetrahydrofuran (350 ml) under nitrogen and the resulting mixture was refluxed for 4 hrs, then cooled to 0° C., and then treated with 10% HCl (150 ml). The mixture was refluxed for 1 hr and cooled, and then the solvent was evaporated. The aqueous residue was basified to pH 11 with 50% NaOH and extracted with chloroform (3×250 ml). The combined chloroform extracts were dried over $MgSO_4$ and evaporated to an oily residue. The residue was dissolved in methanol/isopropanol (150 ml) and acidified with HCl gas. A solid salt crystallized (10.3 g) which was recrystallized from methanol (300 ml) and water (10 ml) to give 9.8 g of cis-1,3,4,6,7,11b-hexahydro-9-methoxy-2-methyl-2H-pyrazino[2,1-a]isoquinoline dihydrochloride as an off-white solid. An analytical sample had mp. 274°–275° C. Following the same procedure and substituting trans-1,3,4,6,7,11b-hexahydro-9-methoxy-2-methyl-6-phenyl-2H-pyrazino[2,1-a]isoquinoline-3,4-dione for cis-1,3,4,6,7,11b-hexahydro-9-methoxy-2-methyl-6-phenyl-2H-pyrazino[2,1-a]isoquinoline-3,4-dione, trans-1,3,4,6,7,11b-hexahydro-9-methoxy-2-methyl-6-phenyl-2H-pyrazino[2,1-a]isoquinoline dihydrochloride may be obtained.

Example 2

Preparation of cis-1,3,4,6,7,11b-hexahydro-9-hydroxy-2-methyl-6-phenyl-2H-pyrazino[2,1-a]isoquinoline dihydrobromide Cis-1,3,4,6,7,11b-hexahydro-9-methoxy-2-methyl-6-phenyl-2H-pyrazino[2,1-a]isoquinoline dihydrochloride (5.0 g, 0.0135 mol) was added with stirring to a solution of 48% HBr (50 ml) under nitrogen and the mixture heated to reflux for 1 hr. The water was then evaporated and the residue triturated, first with toluene (50 ml) and then with acetone (50 ml). The mixture yielded a white solid (7.5 g) which was collected by filtration. This solid was recrystallized from methanol (100 ml) to give 5.24 g (91%) of cis-1,3,4,6,7,11b-hexahydro-9-hydroxy-2-methyl-6-phenyl-2H-pyrazino[2,1-a]isoquinoline dihydrobromide, mp. 259°–260° C. Following the same procedure and substituting trans-1,3,4,6,7,11b-hexahydro-9-methoxy-2-methyl-6-phenyl-2H-pyrazino[2,1-a]isoquinoline dihydrochloride for the cis isomer, trans-1,3,4,6,7,11b-hexahydro-9-hydroxy-2-methyl-6-phenyl-2H-pyrazino[2,1-a]isoquinoline dihydrobromide may be obtained.

Example 3

Preparation of cis-1,3,4,6,7,11b-hexahydro-2-methyl-6-phenyl-2H-pyrazino[2,1-a]isoquinoline dihydrochloride Blended potassium carbonate (15 g) and 5-chloro-1-phenyl-1H-tetrazole (2.24 g, 0.0125 mol) were added with stirring to a solution of cis-1,3,4,6,7,11b-hexahydro-9-hydroxy-2-methyl-6-phenyl-2H-pyrazino[2,1-a]isoquinoline dihydrobromide (5.7 g, 0.012 mol) in dimethyl-sulfoxide (200 ml) under nitrogen and the mixture heated to 40° C. for 4 hrs. The mixture was then poured into water (500 ml) and extracted with ether (3×500 ml). The combined ether extracts were washed with water (3×500 ml), dried over $MgSO_4$ and evaporated to give 4.9 g of the tetrazole alkylated phenol ether. This material was dissolved in absolute ethanol (500 ml) and hydrogenated in a Parr apparatus at 40 psi over 5% palladium on carbon catalyst (2.0 g) for 3 days at 40° C. The catalyst was removed by filtration and then the solvent was evaporated to a residue which was dissolved in chloroform (500 ml), washed with 10% NaOH (3×250 ml), and dried over $MgSO_4$. The solvent was evaporated and the residue dissolved in 50 ml of 1:1 methanol:isopropanol and then acidified with HCl gas. Upon standing, the solution yielded white solid crystals which were collected by filtration and vacuum dried to give 2.3 g of cis-1,3,4,6,7,11b-hexahydro-2-methyl-6-phenyl-2H-pyrazino[2,1-a]isoquinoline dihydrochloride, mp. 270°–271° C. Following the same procedure and substituting trans-1,3,4,6,7,11b-hexahydro-9-hydroxy-2-methyl-6-phenyl-2H-pyrazino[2,1-a]isoquinoline dihydrobromide for the cis isomer, trans-1,3,4,6,7,11b-hexahydro-2-methyl-6-phenyl-2H-pyrazino[2,1-a]isoquinoline may be obtained.

What is claimed is:

1. A compound of the formula

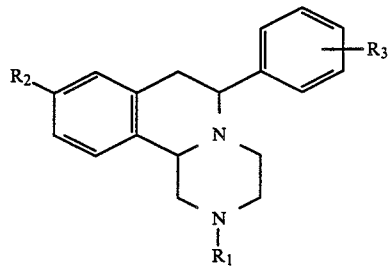

wherein $R_1$ is hydrogen, $C_1$–$C_7$ alkyl, $C_3$–$C_7$ cycloalkyl, or $C_4$–$C_8$ cycloalkylmethyl;

$R_2$ is hydrogen, hydroxy, or $C_1$–$C_7$ alkoxy; and $R_3$ is a single or multiple substitution by hydrogen, hydroxy, halogen, $C_1$–$C_7$ alkoxy, $C_1$–$C_7$ alkyl or trifluoromethyl; all stereoisomeric forms thereof, and pharmaceutically acceptable addition salts thereof.

2. A compound of the formula in claim 1 wherein $R_1$ and $R_2$ are defined as in claim 1 and $R_3$ is a single or double substitution by hydrogen, hydroxy, halogen, $C_1$–$C_7$ alkoxy, $C_1$–$C_7$ alkyl or trifluoromethyl; all stereoisomeric forms thereof, and pharmaceutically acceptable addition salts thereof.

3. A compound of the formula in claim 1 wherein $R_1$ is hydrogen or $C_1$-$C_7$ alkyl; $R_2$ is methoxy, hydroxy or hydrogen; $R_3$ is a single or double substitution by hydrogen, hydroxy, halogen, methoxy, methyl or trifluoromethyl; all stereoisomeric forms thereof, and pharmaceutically acceptable addition salts thereof.

4. The cis diastereoisomeric form of a compound of the formula in claim 1 wherein $R_1$, $R_2$ and $R_3$ are defined as in claim 1; and pharmaceutically acceptable addition salts thereof.

5. The trans-diastereoisomeric form of a compound of the formula in claim 1 wherein $R_1$, $R_2$ and $R_3$ are defined as in claim 1; and pharmaceutically acceptable addition salts thereof.

6. The cis-diastereoisomeric form of the compound of claim 1 wherein $R_1$ is methyl, $R_2$ is methoxy, and $R_3$ is hydrogen, and pharmaceutically acceptable addition salts thereof.

7. The cis-diastereoisomeric form of the compound of claim 1 wherein $R_1$ is methyl, $R_2$ is hydroxy, and $R_3$ is hydrogen, and pharmaceutically acceptable addition salts thereof.

8. The cis-diastereoisomeric form of the compound of claim 1 wherein $R_1$ is methyl, $R_2$ is hydrogen, and $R_3$ is hydrogen, and pharmaceutically acceptable addition salts thereof.

9. A method of treating an allergy comprising the administration of an effective amount of a compound of claim 1 to a mammal in need of such treatment.

10. A method of treating depression comprising the administration of an effective amount of a compound of claim 1 to a mammal in need of such treatment.

* * * * *